United States Patent [19]
Dawson

[11] Patent Number: 5,714,326
[45] Date of Patent: Feb. 3, 1998

[54] METHOD FOR THE MULTIPLEXED PREPARATION OF NUCLEIC ACID MOLECULAR WEIGHT MARKERS AND RESULTANT PRODUCTS

[76] Inventor: Elliott P. Dawson, Box 85, Maple St., Bell Buckle, Tenn. 37020

[21] Appl. No.: 349,471

[22] Filed: Dec. 5, 1994

Related U.S. Application Data

[63] Continuation of Ser. No. 37,704, Mar. 24, 1993, abandoned, which is a continuation of Ser. No. 645,480, Jan. 24, 1991, abandoned.

[51] Int. Cl.$^6$ .............................. C12Q 1/68; C12P 19/34; C07H 21/04; C07H 21/02
[52] U.S. Cl. .............. 435/6; 435/91.2; 536/23.1; 536/24.3; 536/24.32
[58] Field of Search .................. 435/6, 91.2; 536/23.1, 536/24.3–24.33

[56] References Cited

U.S. PATENT DOCUMENTS

| | | | |
|---|---|---|---|
| 4,683,202 | 7/1987 | Mullis | 435/91 |
| 4,889,818 | 12/1989 | Gelfand et al. | 435/194 |
| 5,316,908 | 5/1994 | Carlson et al. | 435/6 |

OTHER PUBLICATIONS

Hartley et al. Nucleotide sequence of the yeast plasmid. Gene (1980) 286:860–865.
Perkin Elmer Cetus, GeneAmp PCR Core Reagents 1991.
Perkin Elmer Cetus, GeneAmp DNA Amplification Reagent Kit 1991.
Yonemura et al. A New Assay Method for DNase by Fluorescence Polarization and Fluorescence . . . J. Biochem. (1982) 92:1297–1303.
Courtens et al. Nucleus of the boar spermatozooa, structure and modifications in frozen, frozen–thawed . . . Mol. Reprod. Dev. (1989) 1:264–277. Abstract.
1989 Bethesda Research Catalogue & Reference Guide, (1989) Life Technologies, Inc., pp. 76–84.
Tung et al. "PCR Amplif. of Specific Seq. from a cDNA Library" in: Erlich, *PCR Technology* (New York, Stockton Press, 1989, pp. 99–104.
Saiki et al. "The Design and Optimization of the PCR" in: Erlich, *PCR Technology* (New York, Stockton Press, 1989, pp. 7–16.

Primary Examiner—W. Gary Jones
Assistant Examiner—Dianne Rees
Attorney, Agent, or Firm—John L. Sigalos

[57] ABSTRACT

A method of making a pool of individual DNA molecular weight markers of defined base pair lengths that are resolved from one another and have substantially equal band intensities and that span the desired range of base pair lengths; the resultant pool of DNA molecular weight markers; the method of determining the presence of a nucleic acid or the length thereof in a specimen suspected of containing a nucleic acid utilizing such resultant pool of markers, and kits utilizing the method of making the pool and/or utilizing the markers.

20 Claims, No Drawings

METHOD FOR THE MULTIPLEXED PREPARATION OF NUCLEIC ACID MOLECULAR WEIGHT MARKERS AND RESULTANT PRODUCTS

This application is a continuation of application Ser. No. 08/037,704, filed Mar. 24, 1993, now abandoned, which is a continuation of application Ser. No. 07/645,480, filed Jan. 24, 1991, now abandoned.

BACKGROUND OF THE INVENTION

Frequently in the field of molecular biology it is necessary to determine the molecular weight (mw) or the base pair (bp) length of nucleic acids. This need encompasses weights or lengths of nucleic acids from sizes ranging from mega bp's down to very short oligonucleotides of only a few bp's. Further the nucleic acids may be single stranded, double stranded, or even triple stranded and may be of either a deoxyribonucleic or ribonucleic acid nature.

Traditionally the base pair length of the nucleic acid has been obtained by comparing the behavior of a nucleic acid under analysis with the behavior of another nucleic acid of defined length and usually but not necessarily of known sequence. Such methods may be electrophoresis, gel filtration chromatography, ultracentrifugation and like methods well known to those in the art. Because of the simplicity of the equipment, ease of use and resolving power to the technique, electrophoresis is the technique most frequently employed to determine the size of nucleic acids.

The standards employed as reference materials for the determination of nucleic acid lengths are often obtained from natural sources. In the case of double stranded DNA these standards are typically prepared from DNA obtained from bacteriophages or plasmids. This process requires the propagation of the virus or plasmid in the appropriate host organism, the purification of the viral or plasmid DNA from the nucleic acids of the host, the digestion of the purified DNA with a restriction endonuclease and the purification of the resulting fragments from undigested DNA and the restriction enzyme. This process is labor, material and equipment intensive, especially for preparation of large quantities of DNA.

Restriction enzyme digested bacteriophage DNA such as that from Lambda and OX174 are frequently employed as molecular weight markers. The array of fragment lengths in bp's obtained depends on the nature of the restriction enzyme, the DNA sequence composition, and the conditions employed. Each combination of restriction enzyme, DNA, and conditions will provide a unique array of DNA fragments of defined lengths. When these fragments are electrophoresed on polyacrylamide, agarose and the like and the resulting gel is stained for DNA, the restriction digested DNA will appear as a ladder of bands. The bands are distributed with the longer bp DNA migrating the shortest distances and the shorter bp DNA migrating the longest distances down the gel under typical conditions well known to those in this art. Depending on the nature of the media, buffers, electrical fields, restriction enzyme and the DNA employed, the fragment bands may be well resolved from one another or be only partially resolved. The observed relative intensities of the bands is directly proportional to the abundance of each fragment and its length. Generally the band intensities diminish as the fragment length decreases. For the analysis of DNA fragments of 3000 bp's or longer adequate standards exist. However, for DNA lengths in the 3000–50 bp range, routinely available standards capable of being resolved into individual fragment bands with sufficient numbers of bands to permit the accurate determination of the bp length of DNA are inadequate.

The recent development of the polymerase chain reaction (PCR) and its consequent application to the fields of molecular biology, genetics, biochemistry, genetic engineering, forensics and the like has caused a reliance on restriction digested DNA as standards for length and molecular weight determination. Reliance on these restriction fragments is problematic. PCR products generally have lengths of from 50 bp to 2500 bp. Electrophoresis is usually conducted on the PCR products to determine if the expected PCR product is present. This is typically accessed by the presence of a band having the expected bp length DNA as the product of the PCR reaction. The presence of the appropriate length DNA in the PCR reaction product is determined by comparison of the product band migration distance to a DNA molecular weight standard. Two restriction enzyme digests have emerged as the most frequently employed for this determination. These are the Hinc II, and Hae III restriction enzyme digests of ØX174. The Hinc II digest of OX174 has 13 bands consisting of fragments of 1057, 770, 612, 495, 392, 345, 341, 335, 297, 291, 210, 162, and 70 bp's in length. The Hae III digest of ØX174 has 11 band consisting of fragments of 1353, 1078, 872, 603, 310, 281, 271, 234, 194, 118, and 72 bp's. All of these digests produce bands of diminishing intensity corresponding to decrease in fragment length. All of these digests have bands which are frequently not resolved under the conditions employed for electrophoresis of PCR products. For example, the cluster of 345, 341, 335 and the cluster of 297, 291 bands of the Hinc II digest ØX174 tend to migrate as single bands as do the cluster of 281 and 271 bands of Hae III digested ØX174. Efforts to overcome some of the problems of DNA digested by a single restriction enzyme include DNA digested by two different restriction enzymes such as the combined Eco RI plus Hind III digest of lambda DNA or the Bgl I plus Hinf I digest of pBR328 DNA, or even the combination of different DNA's digested individually with different restriction enzymes such as the combined Hind III digest of lambda DNA plus the Hae III digest of OX174 DNA have been employed. However, these combinations have similar disadvantages as discussed herein with respect to other digests. The lack of complete resolution, and significantly variable band intensity causes inaccurate DNA length determinations or at best uncertainty of the assignment in some instances. This uncertainty can adversely affect the interpretation and assignment of fragment length analysis of PCR products or for other DNA fragments, particularly in forensic cases.

During development of PCR it may be necessary to apply several concentrations to the gel of marker DNA in order to determine the appropriate concentration of standard in order to obtain standard bands of both adequate resolution and sufficient intensity to permit reliable locations of the expected bp's present in the standards to be established. In instances when the size of the expected PCR product is greater than approximately 500 bp's a small quantity of standard is applied in order to resolve the higher molecular Weight bands from one another in the standard, but this causes the diminishment of intensity of the low molecular weight bands in the standard. In fact, in some instances, the shorter bp length fragments may not even be detectable. On the other hand, when the expected PCR product is of short length a large quantity of standard is applied in order to visualize the shorter bp length bands of sufficient intensity so as to be detected. However, this leads to overloading of the larger bp fragments in the standard causing obscuration of these bands and their poor resolution. Since underloading or overloading the wells affects the band migration of the bands in a given lane, the standards may provide inconsistent fragment length information. Also, the buffer in which the standard is applied to the gel may affect the migration of samples applied in neighboring wells. There has generally been no standardization of the ionic strength of the application solutions for higher standards or samples with respect to PCR products. This inconsistency may occur on the same gel for analysis of replicate specimens, and the same is also true for different specimens.

In PCR, a number of methods have been described for amplifying different targets, obtaining the appropriate length fragment, and the like. Among these are multiplex PCR which permits the generation of a single specific DNA from a single primer and an array of primers. A single product results. A technique employed is the simultaneous amplification within the same tube of non-overlapping sequences which yield two or more products.

No technique has been described, as in the instant invention, which permits use of PCR conditions in which PCR is performed using a single primer (either sense or anti-sense) and an array of primers of opposite strand polarity and distal from one another to produce molecular weight standards of defined length having identical PCR reaction conditions (denaturing, annealing and extension). Further, the instant invention utilizing common reaction components, excepting the noncommon primer, provides products whose product concentrations yield bands well resolved from one another of nearly equal intensity and posses a nearly linear $\log_{10}$ (bp) versus migration distance relationship in agarose, polyacrylaamide or other art-known media or methods employed to determine base pair length employing common buffers.

It is sometimes desirable to have markers bearing a label to facilitate the assignment of bp length to analyzed DNA. Typical markers include radiolabels such $32_P$, $3_H$, $35_S$, $125_I$, $14_C$ and the like or biotin or haptens such as digoxigenin or dinitrophenol. These labels can be incorporated into the existing markers, but the degree of incorporation can be quite variable especially for biotin or digoxigenin, which are typically incorporated by photochemical means.

SUMMARY OF THE INVENTION

A method has now been found of preparing DNA molecular weight markers consisting of an array of defined lengths able to be resolved from one another having substantially equal band intensities, lacking ambiguities of intensities, resolution or identity, capable of incorporating commonly used labels without the requirement for cloning and the elaborate purification process required for present DNA molecular weight markers for the determination of DNA lengths, particulary over the range of 3000 bp to 50 bp.

In this method, as hereinafter described, PCR is employed in an unobvious manner by which a series of molecular weight markers and labeled markers of defined lengths can be prepared which unexpectedly provide for the quantitative incorporation of primers and deoxynucleotide triphosphates. The primer selection process and the conditions set forth for their use permits identical conditions for the thermocycle denaturation, annealing, and extension reactions to be employed for the production of each base pair marker species present in a given series. The method can be scaled up in a linear manner without the appearance of undesired products. The ability to scale up the reaction and the fundamentally identical conditions employed for the thermocycles and the components present in the reaction mixture permits the batch (multiplexed) preparation of the base pair markers in a given series as set forth in the instant application and provides for the preparation of markers in an efficient manner. The results are novel molecular weight markers and their use to determine the length of PCR product. The invention also comprises a kit containing the primers and reagents for the preparation and the condition for its use and a kit containing a series of molecular weight markers.

DETAILED DESCRIPTION

The initial stage is the target selection process.

Suitable targets for the multiplexed production of DNA molecular weight (base pair length) markers are stretches of DNA of sufficient length to permit the selection of regions of defined length spanning the base pair sizes desired in a series. The target material is usually double stranded DNA having a known sequence. The DNA must be able to be obtained in pure form by one of the many techniques widely known in this art. For example, the DNA may be from bacteriophages such as Lambda or ØX174 or from plasmids such as pBR322, pUC18, and the like, the sequences of which are known in this art. Once the target is selected a series of primers are selected having a common downstream primer which is arbitrarily assigned or designated as the "zero length primer" using the selection process discussed below. For convenience, since most DNA sequences are stored in data banks, as their sense (+) strand, the zero length primer is then translated into the sequence having opposite polarity, i.e., antisense or (−). The zero length primer will usually have a length of 18 to 30 bp's and be of opposite strand polarity to the remaining primers defining the base pair series.

Next, the primers defining the base pairs series are selected such that the distance between the 5' end of the zero length primer and the 5' ends of the base pair length primers define the lengths of the products produced by the amplification of the zero length primer and the base pair length primers. For example, if the distance between the 5' end of the zero length primer and the 5' end of the base pair length primer is 100, then the product produced by their amplification is 100 base pairs in length. Further illustrative, a series of base pair length primers spanning the series range of 100 bp, 200 bp, 500 bp, 1000 bp is chosen such that the distance in bp's between the 5' end of the zero and the 5' end of the 100 bp primer is 100 bp's and the primers are of opposite strand polarity and noncomplementary to one another. Likewise, the bp distance between the zero and the 200 bp primer is 200 bp's. The 100 and 200 bp primers have distinct sequences but identical strand polarities, with this process repeated for the selection of 500 and 1000 bp primers. This provides a set of primers having a common origin as defined by the zero length primer, but defining a series of base pair length primers dependent on the selection of the base pair primers and their distance in bp's from their 5' ends and the 5' end of the zero primer.

Prior art primer selection for PCR is usually based on selecting a pair of short DNA sequences of opposite strand polarity spanning a 50 to 4000 bp region of the DNA to be amplified. The primers are typically selected so that the GC content is >50%, but less than 70%, and the primers are selected so as to have approximately identical annealing temperatures. Another aspect of this selection process is that the primers not have structures of three or more repeats of the same base and that the internal complementary of the primer be minimized. Also, the primers should not possess complementary regions at their 3' ends.

In the case of the instant invention, primers are selected in a different manner. They are chosen such that their combined G and C content be 13±2 regardless of length up to 30 bp and that repeats of bases up to 5 in length are permitted. The annealing temperature for PCR is determined by averaging the total GC content of all the primers for a molecular weight series, multiplying this average by 4 and then adding about 5° C. to it.

Primers are synthesized by any of the well known methods for the preparation of synthetic oligonucleotides, such as phosphoramidite, and phosphonate chemistries and the like. The primers may be individually purified by gel electrophoresis or by high pressure liquid chromatography and the like.

The reagents for amplification include a DNA dependent DNA polymerase, usually heat stable deoxynucleotide triphosphates as their sodium, potassium or lithium salts and the like, purified or nearly so target double or single stranded DNA, a pair of primers consisting of a zero length primer and a base pair length primer as described previously above, a suitable buffer compatible with the DNA polymerase employed, and a stabilizing agent. The reaction is performed in buffered aqueous media containing 1.0–4.0 mM $MgCl_2$ (usually 1.5 mM), 0.1% TRITON®, or TWEEN® detergent and the like, 1%–0.1% gelatin, a bovine serum albumin and the like, 10–100 mM KCL (usually 50 mM), and 10–100 mM Tris hydroxyaminoethane buffer (usually 10 mM) at a pH of 7.9–9.0, more usually 8.3–8.8 when measured at 25° C.

The concentration of the deoxynucleotide triphosphates (dATP, dCTP, dGTP, and dTTP are preferred) is usually equimolar to one another and is in the range of 100–500 mM (usually 200 mM) for each dNTP and their purity is typically >90% by HPLC and >80% enzymatically. The DNA polymerase is used at a concentration of approximately 1–3 units per 100 µl, usually 1.5–2.0 units per 100 µl's of reaction volume. The primers are employed at concentrations of 0.5 g per 100 µl of reaction mixture for oligonucleotide primers of 18–30 bases in length.

The reactions are performed in such a manner that the molecular weight marker target is in single stranded form. This may be accomplished by denaturing agents such as NaOH, guanidine hydrochloride, urea and the like or by temperatures between 65° C. and 100° C., usually 93°–97° C. The other reagent components may be present during the denaturation or be added subsequent to denaturation. Denaturation thermocycling as described in U.S. Pat. No. 4,889, 818 is performed. Denaturation by heating at 90°–97° C. for five minutes, usually 94° C. for five minutes, followed by annealing at the annealing temperature, as calculated above, for two minutes by elongation at 70°–75° C. for five minutes, usually 72° C. for 2 minutes. This is followed by 30–35 cycles consisting of denaturing for approximately one minute at 94° C., annealing at the annealing temperature for two minutes, and elongation at 72° C. for two minutes. These cycles are followed by a last elongation step at 72° C. for three to ten minutes, usually five minutes. Following this cycle, the reaction as cooled to 0°–10° C., usually 8° C., for five hours.

Following reaction, the appropriate weight series reactions are separately combined, i.e. all 100 bp reactions are combined, and all 200 bp reactions are separately combined, etc. The mineral oil overlay is pipetted away without removing any of the aqueous reaction mixture. Chloroform is added at a volume 1–2 times that of the remaining oil. This mixture is shaken vigorously, allowed to separate, and then is centrifuged to completely break any emulsion which has formed. An aliquot of each aqueous phase from each bp marker reaction is separately electrophoresed and stained on 2–3% agarose or 7–11% acrylamide using conditions and buffers well known to the art. The reactions are assessed for the equivalent intensity of the bands produced corresponding to the appropriate base pair. To validate the production of the appropriate bp length markers, the reaction products may be sequenced by either the dideoxynucleotide method of Sanger or the chemical method of Maxim and Gilbert. If for any reason one band is of lower intensity, another reaction can be performed to bring the available pool of bp markers to approximately equal concentrations. The bp markers are then pooled by removing the aqueous reaction phase from the lower organic phase for each pool of bp marker reactions to give a set of markers covering the range of the bp's of the marker pool. An antimicrobial is added in conventional amount, such as Thimerisol, Thymol or $NaN_3$ and the like, but usually $NaN_3$. The pool is then frozen at −20° C. and allowed to be frozen for at least one hour to 24 hours, but usually for a period of 12 to 16 hours. Following freezing, the marker set is thawed and centrifuged at approximately 3000×g for 10–15 minutes to compact the precipitate. The precipitate is usually compact enough to permit the aqueous marker phase to be separated therefrom, as by being poured into another container. Electrophoresis is usually performed to verify the band numbers, positions, and intensities and the material then frozen at −20° C. for storage. It may be stored indefinitely in this state. The material may be subjected to several freeze/thaw cycles without degradation. In fact, several freeze/thaw cycles have the observed effect of increasing the intensities of the bands and also appear to bring into balance slight variances in the individual band intensitities to one another.

Non-radioactive labels such as biotin, digoxigenin and DNP may be added to the marker series by adding the appropriate modified dNTP such as biotin-11-dUTP, biotin-dATP, digoxigenin-11-dUTP to the initial reaction material. The labeled dNTP is added such that it represents 10–25%, usually 20% of the concentration of the non-labeled dNTP, i.e. for the labeled dUTP analogs such that it represents 20% of the dTTP concentration and the concentration of the labeled dNTP and its unlabeled equivalents combined are equal to the concentration of each of the remaining unlabeled dNTP's.

Alternatively, photoactive labels can be introduced using any conventional method or the label may be incorporated into the zero length primer for convenience or any of the primers at the time of or following their synthesis by methods well known in this art.

The instant method permits making markers of any base pair lengths desired, or any combination thereof, and having any desired pattern.

A kit can be prepared to produce the bp DNA markers by providing the appropriate primers, enzyme, dNTP's and buffers described above. The kit also contains instructions for the appropriate use of the reagents to produce the bp marker series as described above.

Also, a kit can be provided which contains the prepared, purified bp series preconstituted or in reconstitutable form, tracking dye such as bromophenol blue and necessary instructions. This represents a form in which the marker series is ready to use.

Further, either of the kits described above can be provided so that in the case when the markers are prepared using the kit components suitable labeling materials are provided either in the form of pre-labeled primer, labeled dNTP or labelling agent capable of modifying the produced marker series. When kits are provided with pre-made markers, these markers are provided in labeled form.

The invention will be further described in connection with the following examples which are set forth for purposes of illustration only.

EXAMPLE 1

Deoxyoligonucleotides were synthesized using phosphoramidite chemistry and were obtained from Research Genetics (Huntsville, Ala.). The synthetic olinonucleotides had the sequences and provide the bp lengths specified in Table I when PCR is performed in conjunction with the zero length primer.

TABLE 1

| | |
|---|---|
| 500 bp primer: | 5'-GAT—GAG—TTC—GTG—TCC—GTA—CAA—CTG-3' |
| 400 bp primer: | 5'-CCG—CTC—GCT—GGG—TGA—ACA—A-3' |
| 300 bp priimer: | 5'-ACG—GAT—GAA—ACT—GCC—GGT—CAG—GAC—A-3' |
| 200 bp primer; | 5'-TGG—ATA—CGT—CTG—AAC—TGG—TCA—CGG—T-3' |
| 100 bp primer: | 5'-AAC—GGC—GTT—TCG—TGT—CTC—TGC—CGG—T-3' |
| 0 bp primer: | 3'-CG—CGA—CAC—CGA—CTA—AAG—CTA—TTG-5' |

These sequences were selected from the wild type of lambda phage (Styloviridae) and cover the sequence from 7131–7630 bp Gene Bank accession number J02459 M17233, Locus LAMCG. The 500 bp primer represents the bp region 500 bp's in length from 7131–7630, 400 bp primer represents the region 400 bp's in length from 7231–7630, the 300 bp primer represents the region 300 bp's in length from 6331–7630, the 200 bp primer represents the region from 7431–7630, and the 100 bp primer represents the region from 7531–7630 of the lambda target sequence. The primers were brought into solution using 1 µl of sterile deionized water for every µg of oligonucleotide giving a concentration of 1 µg oligonucleotide/1 µl of solution.

The amplifications were performed using the reaction mixture composition described below. 0.5 µl of the zero primer was added to each of six 0.5 ml microfuge tubes (Perkin Elmer Cetus). The tubes numbered 1–6, with tube #1 receiving 0.5 µl of the 500 bp primer solution, tube #2 receiving 0.5 µl of the 400 bp primer solution, tube #3 receiving 0.5 µl of the 300 bp primer solution, tube #4 receiving 0.5 µl of the 200 bp primer solution, and tube #5 receiving 0.5 µl of the 100 bp primer solution. Tube #6 received 0.5 µl of each of the 100 to 500 bp primer stocks. A stock solution was prepared consisting of 15 µl of each of 10 mM stocks of dATP; dGTP; dCTP and dTTP; 2.5 µl of Taq polymerase (5000 units/ml stock); 60 µl of a 500 mM KCl, 100 mM Tris-HCl, pH 8.3; 0.1% gelatin, 15 mM MgCl$_2$ solution and 540 µl of sterile deionized water. 100 µl of this stock mixture was added to each tube. Tube #6 was layered with 100 µl of mineral oil (Sigma) and closed. lng of lambda DNA was then added to tubes #1–5, no lambda DNA was added to tube #6. The tubes were layered with 100 µl oil and closed. Tubes #1–6 were then placed in the oil wetted wells of a thermocycler (GENE AMP—Perkin Elmer Cetus).

The first thermocycle consisted of one round of heating to 94° C. for 5 minutes, cooling rapidly (@ 1° C./second) to 56° C. for 2 minutes and then rapidly heating (@1° C./second) to 72° C. for 2 minutes. This was immediately followed by heating rapidly to 94° C., maintaining 94° C. for 1 minute, cooling rapdily to 56° C., maintaining 56° C. for 2 minutes, heating rapidly to 72° C., and maintaining 72° C. for 2 minutes. This cycle was repeated 29 more times. Following the last cycle the tubes were immediately maintained at 72° C. for a further 7 minutes, then rapidly cooled to 8° C. and left overnight at this temperature.

Electrophoresis of 1 µl aliquots of each reaction mixture on 3% agarose gel using 0.5×TBE indicates the presence of product in tubes #1–5 and no product, as expected, in tube #6. The length of the products was estimated by comparison to the bands present in Hinc II and Hae III digest ØX174. The bands present in tubes #1–5 correspond to bp lengths of 500, 400, 300, 200 and 100 bp's, as expected.

The migration distances of the respective products of tubes #1–5 were determined from their application points. A least squares regression analysis of the log$_{10}$ (bp) length vs. migration distance gave a correlation coefficient of 0.98 (Lotus 123, Lotus Development Corp.).

The reaction products were purified by pipetting away the mineral oil overlay without removing any of the reaction mixture. The remaining mineral oil was then carried to a lower layer by the addition of 100 µl of chloroform and mixing. The tubes were then centrifuged at 3000×g for 5 minutes. The aqueous reaction phase (upper) was removed and combined. A 5 µl aliquot of the combined material was electrophoresed and no change in the band migration pattern or band intensities was observed following ethidium bromide staining and photographing the gel.

The combined bp marker material was then frozen at −20° C. and left for 16 hours (overnight) at this temperature. It was thawed and a precipitate was removed by centrifuging the pooled reaction mixtures at 3000×g for 10 minutes and decanting and saving the aqueous phase and discarding the precipitate. The recovered aqueous phase containing the bp marker series was made 0.01% NaN$_3$ by addition of NaN$_3$ to prevent microbial growth. This material was stored frozen at −20° C. and subjected to 20 freeze/thaw cycles. Electrophoresis of aliquots saved from each purification step and the freeze/thaw cycled material indicated no deterioration of the material.

When the bp length markers covering the range of 500–100 were employed as standards for the measurement of bp length in PCR products of known length, the comparison of the migration distances of these products with the migration distances of the bp length standards consistently gave values within 2 bp's of the true values for these PCR products. The bp lengths of the known PCR products were 500, 484, 98, and 95 bp's. The values computed from the comparison of migration distances with the standards were 500, 483, 97 and 93 bp's respectively.

EXAMPLE 2

The procedure of Example 1 was employed except that primers corresponding to 700 bp's and 1000 bp's were included in the reaction series and the reagents were proportionately increased. This produced a series of bp markers corresponding to 1000, 700, 500, 400, 300, 200, and 100 bp's. The sequences of the 700 bp primer and the 1000 bp primer are provided below.

| | |
|---|---|
| 700 bp primer | 5'-TCC—TGC—CGC—ACA—ACA—CGA—TG-3' |
| 1000 bp primer | 5'-GCG—GCA—CGG—AGT—GGA—GCA—AG-3' |

These primers represent the regions of 6931–7630 and 6631–7630 bp's of lambda phage, respectively.

Equally good results are obtained after testing as in Example 1.

EXAMPLE 3

The procedure of Example 1 was followed except that primers corresponding to 3000, 2500, 2000, 1500 and 1000 bp's were employed and an annealing temperature of 54° C., and extenstion times were increased by one minute, with the reagent concentrations being adjusted proportionate to the number of reactions performed.

The sequences of the primers is given below:

| | |
|---|---|
| 3000 bp | 5'-CAG—GCC—CGC—AGT—TAT—CAG—GTC-3' |
| 2500 bp | 5'-AGG—GTG—TGG—AAA—TCA—CGC—TG-3' |
| 2000 bp | 5'-GCA—GTG—ACA—CTG—CGC—TGG—ATC-3' |
| 1500 bp | 5'-TTT—TAT—GTC—GAT—GTA—CAC—AAC—CGC—CCA-3' |
| 1000 bp | As per Example 2 above. |

The 3000, 2500, 2000 and 1500 bp primers represent the regions of 4631–7630, 5031–7630, 5631–7630 and 6131–7630 bp's of lambda phage, respectively.

These are tested as in Example 1 and equally good results are obtained.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method of producing DNA standards that comprise a pool of at least two individual linear double-stranded DNA molecules of different and definite lengths that are resolved from one another when fractioned by electrophoresis; wherein each said individual DNA molecules is present in said pool in substantially equal concentration based on a determination of units of mass per unit of volume of one individual DNA molecule relative to units of mass per unit volume of another individual DNA molecule and wherein said individual DNA molecules produce substantially equal measurable signals when said molecules are detectably labeled, said method comprising:

(a) selecting a common primer of 15 to 30 bases in length complementary to a specific region of a target DNA molecule, and at least two different primers of 15 to 30 bases in length which differ in sequence from said common primer and which are complementary to the target DNA molecule if said target DNA molecule is double-stranded or are complementary to an extension product of the common primer formed by polymerase chain reaction, if said target DNA molecule is single-stranded;

(b) performing polymerase chain reaction in separate mixtures, each mixture containing one said common primer with one of said at least two different primers, and forming individual linear double-stranded DNA in each mixture wherein the length of an individual DNA linear double-stranded DNA molecule formed in any one mixture is different from the length of an individual double-stranded DNA molecule formed in any other mixture;

(c) purifying individual linear double-stranded DNA molecules formed in each mixture to obtain an aqueous phase for each mixture containing said individual linear double-stranded DNA molecules;

(d) combining at least two different aqueous phases to provide substantially equal concentrations of individual double-stranded DNA molecules of different length based on a determination of units of mass per unit of volume of different individual double-stranded DNA molecules within said aqueous phase, to form a pool of said different individual double-stranded DNA molecules at substantially equal concentrations;

(e) subjecting said pool to at least one cycle of freeze-thawing; and (f) adding an effective amount of an antimicrobial to said pool to prevent microbial growth.

2. The method of claim 1 wherein prior to pooling said individual linear double stranded DNA's are labeled.

3. The method of claim 2 wherein the desired range of of DNA lengths is from 50 to 3000 base pairs.

4. A pool of individual double-stranded linear DNA molecules generated by the method of claim 1, wherein said individual double-stranded linear DNA molecules are of different and definite lengths having substantially equal band intensities when labeled with a detectable label and span the desired range of base pair lengths.

5. A method of determining the size of a nucleic acid in a specimen suspected of containing a nucleic acid comprising fractionating said specimen by electrophoresis utilizing as a reference standard the pool of individual double stranded DNA's molecules of claim 4.

6. A kit for carrying out the method of claim 5 comprising the pool of individual double stranded DNA's of claim 4 and a tracking dye.

7. A pool of individual double-stranded linear DNA molecules generated by the method of claim 2, wherein said individual double stranded linear DNA molecules are of different and definite lengths having substantially equal band intensities when labeled with a detectable label and span the desired range of base pair lengths.

8. A pool of individual double-stranded linear DNA molecules generated by the method of claim 3, wherein said individual linear double stranded DNA molecules are of different and definite lengths having substantially equal band intensities when labeled with a detectable label and span the desired range of base pair lengths.

9. A method of determining the size of a nucleic acid in a specimen suspected of containing a nucleic acid comprising fractionating said specimen by electrophoresis utilizing as a reference standard the pool of individual double-stranded molecules DNA of claim 7.

10. A method of determining the size of a nucleic acid in a specimen suspected of containing a nucleic acid comprising fractionating said specimen by electrophoresis utilizing as a reference standard the pool of individual double-stranded molecules DNA of claim 8.

11. A kit for carrying out the method of claim 5 comprising the pool of individual double stranded DNA molecules of claim 9 and a tracking dye.

12. A kit for carrying out the method of claim 5 comprising the pool of individual double stranded DNA molecules of claim 10 and a tracking dye.

13. The method of claim 1, including the step of adding a label to said DNA molecules.

14. The method of claim 13 wherein said label is a non-radioactive label.

15. The method of claim 13 wherein said non-radioactive label is biotin, digoxigenin, or dinitrophenol.

16. The pool of claim 4, wherein the individual double-stranded molecules are generated by the method of claim 13.

17. The pool of claim 16, wherein the label is biotin, digoxigenin, or dinitrophenol.

18. The method of claim 10, including the step of adding a label to said DNA molecules.

19. The kit of claim 12, wherein the DNA molecules are labeled.

20. The kit of claim 19, wherein the label is biotin, digoxigenin, or dinitrophenol.

* * * * *

UNITED STATES PATENT AND TRADEMARK OFFICE
CERTIFICATE OF CORRECTION

PATENT NO : 5,714,326
DATED : February 3, 1998
INVENTOR(S): Elliott P. Dawson

It is certified that error appears in the above-identified patent and that said Letters Patent is hereby corrected as shown below:

Column 5, line 27, after TRITON® insert --X-100 (a non-ionic heterogenous phenoxypolyoxyethylene ether)--; and line 27, after TWEEN® insert --20 (non-ionic polyoxyethylene sorbitan derivative of a fatty acid) --.

Signed and Sealed this

Twenty-sixth Day of May, 1998

Attest:

BRUCE LEHMAN

*Attesting Officer*           *Commissioner of Patents and Trademarks*